United States Patent [19]

Kawata et al.

[11] Patent Number: 4,668,615
[45] Date of Patent: May 26, 1987

[54] HEAT DEVELOPABLE LIGHT-SENSITIVE MATERIAL

[75] Inventors: Ken Kawata; Yoshiharu Yabuki; Kozo Sato; Hiroyuki Hirai, all of Kanagawa, Japan

[73] Assignee: Fuji Photo Film Co., Ltd., Kanagawa, Japan

[21] Appl. No.: 767,981

[22] Filed: Aug. 21, 1985

[30] Foreign Application Priority Data

Aug. 21, 1984 [JP] Japan .................. 59-173889

[51] Int. Cl.$^4$ .................. G03C 1/40; G03C 5/54; G03C 1/06
[52] U.S. Cl. .................. 430/617; 430/151; 430/171; 430/180; 430/955; 430/559; 430/561; 430/562; 430/541; 430/619; 430/620; 430/351; 430/353; 430/495; 430/203; 430/570
[58] Field of Search ........... 430/617, 619, 620, 570, 430/560, 203, 151, 955, 177, 180, 541, 495, 351, 353

[56] References Cited

U.S. PATENT DOCUMENTS

| | | | |
|---|---|---|---|
| 3,220,846 | 11/1965 | Tinker et al. | 430/346 |
| 4,487,826 | 12/1984 | Watanabe et al. | 430/151 |
| 4,499,172 | 2/1985 | Hirai et al. | 430/619 |
| 4,514,493 | 4/1985 | Hirai et al. | 430/619 |

FOREIGN PATENT DOCUMENTS 909491 10/1962 United Kingdom ............ 430/151

*Primary Examiner*—Won H. Louie
*Attorney, Agent, or Firm*—Sughrue, Mion, Zinn, Macpeak & Seas

[57] ABSTRACT

A heat developable light-sensitive material containing a compound represented by the general formula (I):

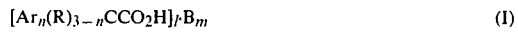

$$[Ar_n(R)_{3-n}CCO_2H]_l \cdot B_m \qquad (I)$$

wherein ar represents an aryl group or a heterocyclic group; R represents a substituent other than an aryl group and a heterocyclic group; Ar and R may be bonded in a part thereof to form a ring; B represents a mono- or diacidic base which has a pKa of 7 or more and contains 12 or less carbon atoms; n represents an integer from 1 to 3; l and m each represents an integer of 1 or 2 and maintain a relationship in that a number of positive charge and a number of negative charge are equal; when n represents 1 or 2, two R's or Ar's may be the same or different, when n represents 3, three Ar's may be the same or different; and the substituent represented by Ar or R may be further substituted with a substituent. The compound represented by the general formula (I) is a base precursor which is stable at normal temperature but rapidly decomposes to release a base by heating and therefore the heat developable light-sensitive material containing the base precursor has excellent preservability and provides images having good image quality, i.e., low fog density and high image density upon a short period of developing time.

20 Claims, No Drawings

HEAT DEVELOPABLE LIGHT-SENSITIVE MATERIAL

FIELD OF THE INVENTION

The present invention relates to a heat developable light-sensitive material. More particularly, the present invention relates to a heat developable light-sensitive material containing a novel base precursor.

BACKGROUND OF THE INVENTION

It is generally desirable to employ a base in a heat developable light-sensitive material in order to accelerate development by heat. In order to increase stability of the light-sensitive material, it is necessary to employ the base in the form of a precursor. The term "precursor" as used herein means a compound which thermally decomposes and releases a basic component by heating. In order to employ such a precursor in practical use, it is necessary that the precursor have two opposite properties, i.e., stability at normal temperature (about 0° C. to 35° C.) and rapid decomposability at the time of heating.

Basic precursors which have been heretofore known include, for example, a urea as described in U.S. Pat. No. 2,732,299 and Belgian Pat. No. 625,554, a method using urea or urea and an ammonium salt of a weak acid as described in Japanese Patent Publication No. 1699/65, a method using hexamethylenetetramine or semicarbazide (as described in U.S. Pat. No. 3,157,503), a method using a triazine compound and a carboxylic acid (as described in U.S. Pat. No. 3,493,374), a dicyandiamide derivative (as described in U.S. Pat. No. 3,271,155), an N-sulfonyl urea (as described in U.S. Pat. No. 3,420,665), an aminimido (as described in *Research Disclosure*, RD-15776 (1977)), and a salt of a thermally decomposable acid represented by trichloroacetate (as described in British Pat. No. 998,949), etc.

However, image forming materials using these base precursors have essentially serious defects. Specifically, these compounds cannot fulfill the above described indispensable conditions, i.e., good stability during preservation at normal temperature and rapid decomposition at the time of development processing, and cause problems in that a high image density cannot be obtained or the S/N ratio of image is seriously decreased due to release of the base during preservation.

SUMMARY OF THE INVENTION

Therefore, an object of the present invention is to provide a heat developable light-sensitive material which is excellent in stability during preservation and which can reproduce an image of high quality.

Another object of the present invention is to provide a heat developable light-sensitive material containing a novel base precursor which is particularly effective to provide an image having a high density and low fog.

A further object of the present invention is to provide a heat developable light-sensitive material which can form an image having a high density in a short period of time.

These and other objects of the present invention will become more apparent from the following detailed description and examples.

These objects of the present invention are accomplished with a heat developable light-sensitive material containing a compound represented by the general formula (I):

$$[Ar_n(R)_{3-n}CCO_2H]_l \cdot B_m \quad (I)$$

wherein Ar represents an aryl group or a heterocyclic group; R represents a substituent other than an aryl group and a heterocyclic group; Ar and R may be bonded in a part thereof to form a ring; B represents a mono- or diacidic base which has a pKa of 7 or more and contains 12 or less carbon atoms; n represents an integer from 1 to 3; l and m each represents an integer of 1 or 2 and maintain a relationship in that a number of positive charge and a number of negative charge are equal; when n represents 1 or 2, two R's or Ar's may be the same or different, when n represents 3, three Ar's may be the same or different; and the substituent represented by Ar or R may be further substituted with a substituent.

DETAILED DESCRIPTION OF THE INVENTION

In the compound represented by the general formula (I), the aryl group or the heterocyclic group represented by Ar may be substituted as described above. Particularly, those groups having an electron withdrawing group having a Hammett's $\sigma$ value of 0 or greater (for example, a halogen atom, a nitro group, a cyano group, an acyl group, etc.) as a substituent are preferred.

Specific examples of preferred groups represented by Ar include the following:

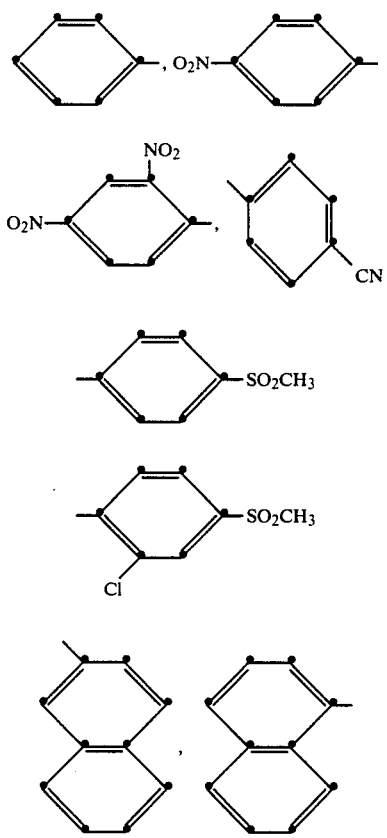

-continued

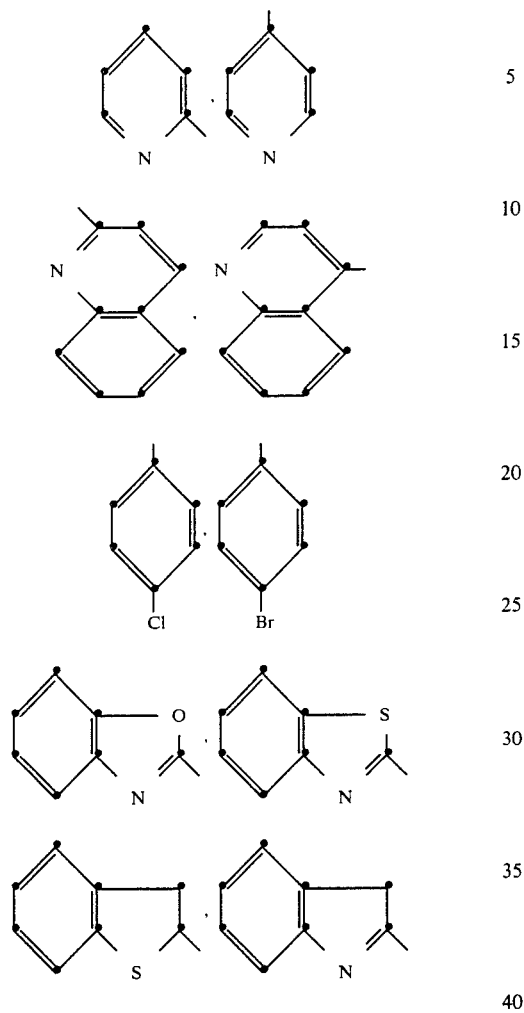

The substituent represented by R include a hydrogen atom, a silyl group, an alkyl group, an alkenyl group, an alkynyl group, an aralkyl group, a cycloalkyl group, an alkoxy group, an aryloxy group, an alkylthio group, an arylthio group and a hydroxy group. The alkyl moiety and aryl moiety included in these substituents may be further substituted, for example, with a silyl group, an alkyl group, an alkenyl group, an alkynyl group, an aralkyl group, a cycloalkyl group, an alkoxy group, an aryloxy group, an alkylthio group, an arylthio group and a hydroxy group.

Ar and R may be bonded in a part thereof to form a ring and examples of such ring are shown in Base Precursors (11), (12), (13) and (14) as described hereinafter.

The base portion represented by B includes an organic base which has a pKa of 7 or more and contains 12 or less carbon atoms. Among them, those having a pKa of 9 or more and a boiling point of 100° C. or higher are preferred, and those having a pKa of 10 or more and being substantially nonvolatile at normal temperature and free from a bad smell are particularly preferred. Examples of particularly preferred organic bases include guanidines, cyclic guanidines, amidines, cyclic amidines, etc. Further, the base portion B desirably is hydrophilic and those having 10 or less as the total number of carbon atoms are preferably employed. In the following, preferred examples of the base portion B are set forth.

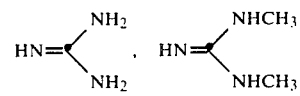

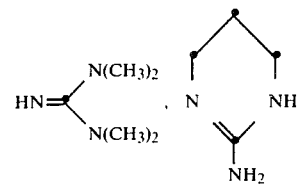

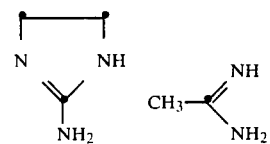

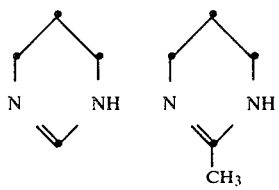

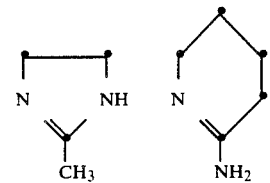

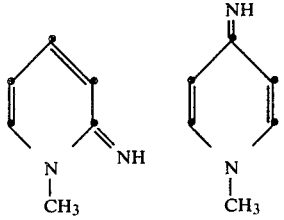

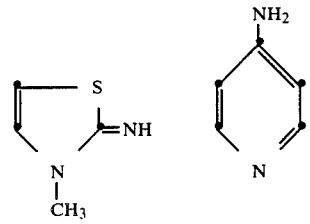

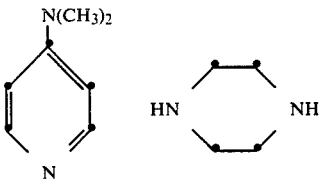

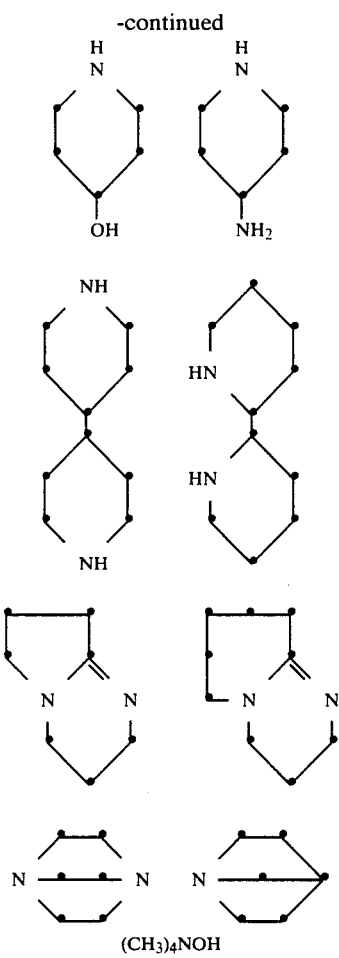

(CH₃)₄NOH

The base precursor which is used in the present invention is characterized by its structure in that the α-position of the carboxy group corresponds to a benzyl position. By this structural characteristic the carboxy group is very easily subjected to decarboxylation. However, the base precursor according to the present invention is extremely stable at normal temperature and does not release a base component until upon decarboxylation by means of heating. As a result, it is possible to fulfill two opposite properties required to base precursors, i.e., stability during preservation at normal temperature and rapid decomposition (release of base) at the time of development processing. Therefore, by the use of the base precursors according to the present invention, it becomes possible to provide an excellent heat developable image forming material in which the known drawbacks are eliminated.

The base precursor according to the present invention can be used in an amount of a broad range. It is suitably used in an amount of 50% by weight or less, and more preferably in a range from 0.01% by weight to 40% by weight, based on the coated amount of a layer of the light-sensitive material.

Specific examples of the base precursors used in the present invention are set forth below, but the present invention is not to be construed as being limited thereto.

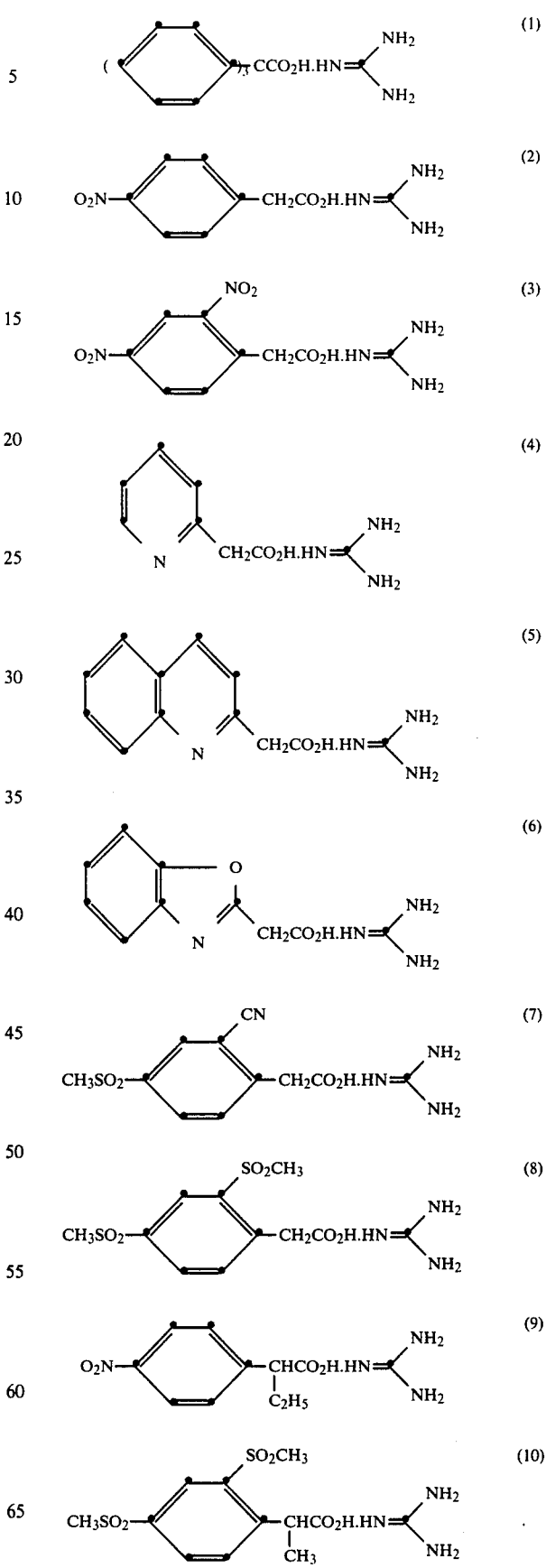

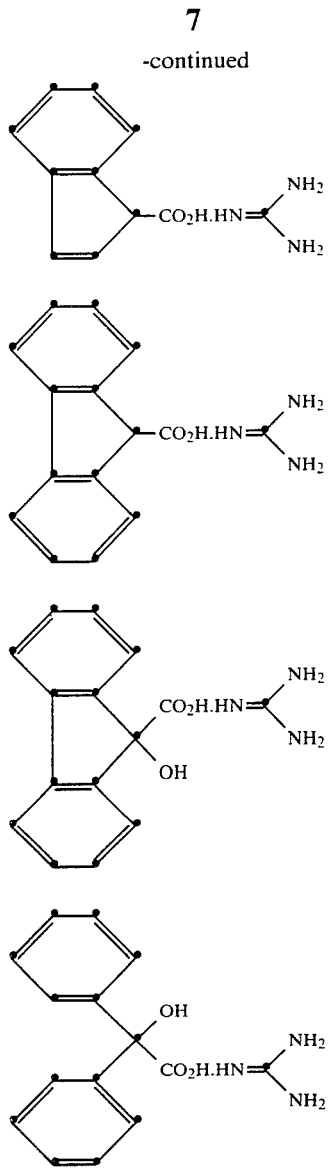

With respect to the representative base precursor used in the present invention, a synthesis example thereof is illustrated below.

SYNTHESIS EXAMPLE

Synthesis of Base Precursor (1)

To 400 ml of ether were added 15 g of magnesium (flaked) and 3.2 g of iodine. 27.9 g of triphenylchloromethane was carefully added thereto and the mixture was refluxed by heating for 3 hours. To the reaction solution was gradually added a large excess of dry ice. The reaction solution was acidified with hydrochloric acid and then extracted with ethyl acetate. After distilling off the solvent, the crystals thus obtained were recrystallized from ethanol to obtain 16.5 g of triphenylacetic acid. The melting point was 258° to 260° C. (decomposed).

A mixture of 8.4 g of triphenylacetic acid thus obtained and 25 ml of methanol was neutralised by adding an aqueous solution containing 2.6 g of guanidine carbonate. After stirring the mixture for 2 hours, the crystals thus formed were collected by filtration to obtain 9.2 g of Base Precursor (1). The melting point was 237° to 238° C. (decomposed).

Other base precursors than Base Precursor (1) can be synthesized by various methods. The melting points of Base Precursors (2) and (3) are 163° to 165° C. (decomposed) and 122° to 125° C. (decomposed), respectively.

The base precursor according to the present invention is preferably used in the form of a salt from the beginning. However, it may be prepared to use in a binder by neutralizing the acid portion and the base portion.

The base precursor according to the present invention remarkably exhibits its effects when it is employed with a silver halide emulsion as a light-sensitive substance.

According to the present invention, silver can be utilized as an image forming substance. Further, various other image forming substances can be employed in various image forming processes.

For instance, couplers capable of forming color images upon reaction with an oxidation product of a developing agent which are used in liquid development processing widely known hitherto can be employed. For example, as magenta couplers, there are 5-pyrazolone couplers, pyrazolobenzimidazole couplers, cyanoacetylcoumarone couplers and open chain acylacetonitrile couplers, etc. As yellow couplers, there are acylacetamide couplers (for example, benzoylacetanilides and pivaloyacetanilides), etc. As cyan couplers, there are naphthol couplers and phenol couplers, etc. It is preferred that these couplers be nondiffusible substances which have a hydrophobic group called a ballast group in the molecule thereof or be polymerized substances. The couplers may be any of the 4-equivalent type and 2-equivalent type to silver ions. Further, they may be colored couplers having a color correction effect or couplers which release a development inhibitor at development processing (so-called DIR couplers).

Further, dyes for forming positive color images by a light-sensitive silver dye bleach processes, for example, those as described in Research Disclosure, No. 14433, pages 30–32 (April, 1976), ibid., No. 15227, pages 14–15 (December, 1976) and U.S. Pat. No. 4,235,957, etc., can be employed.

Moreover, leuco dyes as described, for example, in U.S. Pat. Nos. 3,985,565 and 4,022,617, etc., can be used.

Further, dyes to which a nitrogen-containing heterocyclic group have been introduced as described in Research Disclosure, No. 16966, pages 54–58 (May, 1978), may be employed.

In addition, dye providing substances which release a mobile dye by utilizing a coupling reaction of a reducing agent oxidized by an oxidation reduction reaction with a silver halide or an organic silver salt at high temperature as described in European Pat. No. 79,056, West German Pat. No. 3,217,853, European Pat. No. 67,455, etc., and dye providing substances which release a mobile dye as a result of an oxidation reduction reaction with a silver halide or an organic silver salt at high temperature as described in European Pat. No. 76,492A, West German Pat. No. 3,215,485, European Pat. No. 66,282, Japanese Patent Application Nos. 28928/83 and 26008/83, etc., can be employed.

Preferred dye providing substances which can be employed in these processes can be represented by the following general formula (CI):

$$(Dye-X)_q-Y \qquad (CI)$$

wherein Dye represents a dye which becomes mobile when it is released from the molecule of the compound represented by the general formula (CI); X represents a simple bond or a connecting group; Y represents a group which releases Dye in corresondence or counter-correspondence to light-sensitive silver salts having a latent image distributed imagewise, the diffusibility of Dye released being different from that of the compound represented by formula (CI) and q represents an integer of 1 or 2.

The dye represented by Dye is preferably a dye having a hydrophilic group. Examples of the dye which can be used include azo dyes, azomethine dyes, anthraquinone dyes, naphthoquinone dyes, styryl dyes, nitro dyes, quinoline dyes, carbonyl dyes and phthalocyanine dyes, etc. These dyes can also be used in the form of having temporarily shorter wavelengths, the color of which is recoverable in the development processing.

More specifically, the dyes as described in European Pat. No. 76,492A can be utilized.

Examples of the connecting group represented by X include —NR— (wherein R represents a hydrogen atom, an alkyl group, or a substituted alkyl group), —SO$_2$—, —CO—, an alkylene group, a substituted alkylene group, a phenylene group, a substituted phenylene group, a naphthylene group, a substituted naphthylene group, —O—, —SO—, or a group derived by combining together two or ore of the foregoing groups.

In the following, preferred embodiments of Y in formula (CI) are described in greater detail.

In one embodiment, Y is selected so that the compound represented by the general formula (CI) is a nondiffusible image forming compound which is oxidized as a result of development, thereby undergoing self-cleavage and releasing a diffusible dye.

An example of Y which is effective for compounds of this type is an N-substituted sulfamoyl group. For example, a group represented by formula (CII) is illustrated for Y.

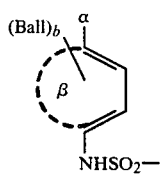
(CII)

wherein
β represents non-metallic atoms necessary for forming a benzene ring, which may optionally be fused with a carbon ring or a hetero ring to form, for example, a naphthalene ring, a quinoline ring, a 5,6,7,8-tetrahydronaphthalene ring, a chroman ring or the like;
α represents a group of —OG$^{11}$ or —NHG$^{12}$ (wherein G$^{11}$ represents hydrogen or a group which forms a hydroxyl group upon being hydrolyzed, and G$^{12}$ represents hydrogen, an alkyl group containing 1 to 22 carbon atoms or a hydrolyzable group);
Ball represents a ballast group; and
b represents an integer of 0, 1 or 2.

Specific examples of this type of Y are described in Japanese Patent Application (OPI) Nos. 33826/73 and 50736/78.

Other examples of Y suited for this type of compound are those represented by the following general formula (CIII):

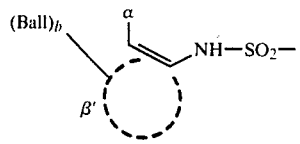
(CIII)

wherein Ball, α and b are the same as defined with (CII), β' represents atoms necessary for forming a carbon ring (e.g., a benzene ring which may be fused with another carbon ring or a hetero ring to form a naphthalene ring, quinoline ring, 5,6,7,8-tetrahydronaphthalene ring, chroman ring or the like. Specific examples of this type of Y are described in Japanese Patent Application (OPI) Nos. 113624/76, 12642/81, 16130/81, 4043/82 and 650/82 and U.S. Pat. No. 4,053,312.

Further examples of Y suited for this type of compound are those represented by the following formula (CIV):

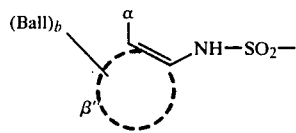
(CIV)

wherein Ball, α and b are the same as defined with the formula (CII), and β" represents atoms necessary for forming a hetero ring such as a pyrazole ring, a pyridine ring or the like, said hetero ring being optionally bound to a carbon ring or a hetero ring. Specific examples of this type of Y are described in Japanese Patent Application (OPI) No. 104343/76.

Still further examples of Y suited for this type of compound are those represented by the following formula (CV):

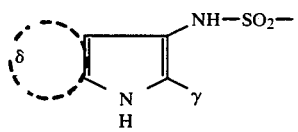
(CV)

wherein γ preferably represents hydrogen, a substituted or unsubstituted alkyl, aryl or heterocyclic group, or —CO—G$^{21}$; G$^{21}$ represents —OG$^{22}$, —SG$^{22}$ or

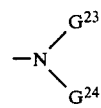

(wherein G$^{22}$ represents hydrogen, an alkyl group, a cycloalkyl group or an aryl group, G$^{23}$ is the same as defined for said G$^{22}$, or G$^{23}$ represents an acyl group derived from an aliphatic or aromatic carboxylic or sulfonic acid, and G$^{24}$ represents hydrogen or an unsubstituted or substituted alkyl group); and δ represents a residue necessary for completing a fused benzene ring.

Specific examples of this type of Y are described in Japanese Patent Application (OPI) Nos. 104343/76, 46730/78, 130122/79 and 85055/82.

Still further examples of Y suited for this type of compound are those represented by the formula (CVI):

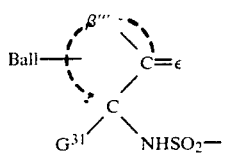
(CVI)

wherein Ball is the same as defined with the formula (CII); $\epsilon$ represents an oxygen atom or $=NG^{32}$ (wherein $G^{32}$ represents hydroxyl or an optionally substituted amino group) (examples of $H_2N-G^{32}$ to be used for forming the group of $=NG^{32}$ including hydroxylamine, hydrazines, semicarbazides, thiosemicarbazides, etc.); $\beta'''$ represents a saturated or unsaturated nonaromatic 5-, 6- or 7-membered hydrocarbon ring; and $G^{31}$ represents hydrogen or a halogen atom (e.g., a fluorine atom, a chlorine atom, a bromine atom, etc.).

Specific examples of this type of Y are described in Japanese Patent Application (OPI) Nos. 3819/78 and 48534/79.

Other examples of Y of this type of compound are described in Japanese Patent Publication Nos. 32129/73, 39165/73, Japanese Patent Application (OPI) No. 64436/74, U.S. Pat. No. 3,443,934, etc.

Still further examples of Y are those represented by the following formula (CVII):

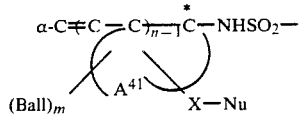
(CVII)

wherein $\alpha$ represents $OR^{41}$ or $NHR^{42}$; $R^{41}$ represents hydrogen or a hydrolyzable component; $R^{42}$ represents hydrogen, or an alkyl group containing 1 to 50 carbon atoms; $A^{41}$ represents atoms necessary for forming an aromatic ring; Ball represents an organic immobile group existing on the aromatic ring, with Ball's being the same or different from each other; m represents an integer of 1 or 2; X represents a divalent organic group having 1 to 8 atoms, with the nucleophilic group (Nu) and an electrophilic center (asterisked carbon atom) formed by oxidation forming a 5- to 12-membered ring; Nu represents a nucleophilic group; n represents an integer of 1 or 2; and $\alpha$ may be the same as defined with the above described formula (CII). Specific examples of this type of Y are described in Japanese Patent Application (OPI) No. 20735/82.

As still further type of examples represented by the formula (CI), there are dye providing nondiffusible substances which release a diffusible dye in the presence of a base as a result of self cyclization or the like but which, when reacted with an oxidation product of a developing agent, substantially never release the dye.

Examples of Y effective for this type of compound are those which are represented by the formula (CVIII):

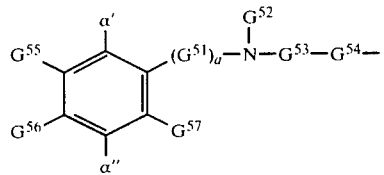
(CVIII)

wherein
$\alpha'$ represents an oxidizable nucleophilic group (e.g., a hydroxy group, a primary or secondary amino group, a hydroxyamino group, a sulfonamido group or the like) or a precursor thereof;
$\alpha''$ represents a dialkylamino group or an optional group defined for $\alpha'$;
$G^{51}$ represents an alkylene group having 1 to 3 carbon atoms;
a represents 0 or 1;
$G^{52}$ represents a substituted or unsubstituted alkyl group having 1 to 40 carbon atoms or a substituted or unsubstituted aryl group having 6 to 40 carbon atoms;
$G^{53}$ represents an electrophilic group such as $-CO-$ or $-CS-$;
$G^{54}$ represents an oxygen atom, a sulfur atom, a selenium atom, a nitrogen atom or the like and, when $G^{54}$ represents a nitrogen atom, it has hydrogen or may be substituted by an alkyl or substituted alkyl group having 1 to 10 carbon atoms or an aromatic residue having 6 to 20 carbon atoms; and
$G^{55}$, $G^{56}$ and $G^{57}$ each represents hydrogen, a halogen atom, a carbonyl group, a sulfamyl group, a sulfonamido group, an alkyloxy group having 1 to 40 carbon atoms or an optional group defined for $G^{52}$, $G^{55}$ and $G^{56}$ may form a 5- to 7-membered ring, and $G^{56}$ may represent

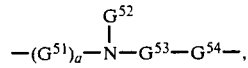

with the proviso that at least one of $G^{52}$, $G^{55}$, $G^{56}$ and $G^{57}$ represents a ballast group. Specific examples of this type of Y are described in Japanese Patent Application (OPI) No. 63618/76.

Further examples of Y suited for this type of compound are those which are represented by the following general formulae (CIX) and (CX):

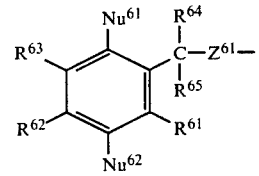
(CIX)

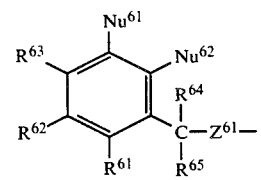
(CX)

wherein $Nu^{61}$ and $Nu^{62}$, which may be the same or different, each represents a nucleophilic group or a precursor thereof; $Z^{61}$ represents a divalent atom group which is electrically negative with respect to the carbon atom substituted by $R^{64}$ and $R^{65}$; $R^{61}$, $R^{62}$ and $R^{63}$ each represents hydrogen, a halogen atom, an alkyl group, an alkoxy group or an acylamino group or, when located at adjacent positions on the ring, $R^{61}$ and $R^{62}$ may form a fused ring together with the rest of the molecule, or $R^{62}$ and $R^{63}$ may form a fused ring together with the rest of the molecule; $R^{64}$ and $R^{65}$, which may be the same or different, each represents hydrogen, a hydrocarbon group or a substituted hydrocarbon group; with at least one of the substituents, $R^{61}$, $R^{62}$, $R^{63}$, $R^{64}$ and $R^{65}$ having a ballast group, Ball, of an enough size so as to render the above described compounds immobile. Specific examples of this type of Y are described in Japanese Patent Application (OPI) Nos. 69033/78 and 130927/79.

Further examples of Y suited for this type of compound are those which are represented by the formula (CXI):

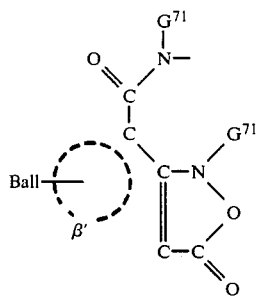
(CXI)

wherein Ball and $\beta'$ are the same as defined for those in formula (CIII), and $G^{71}$ represents an alkyl group (including a substituted alkyl group). Specific examples of this type of Y are described in Japanese Patent Application (OPI) Nos. 11628/74 and 4819/77.

As different type of compound represented by the general formula (CI), there are illustrated dye providing nondiffusible substances which themselves do not release any dye but, upon reaction with a reducing agent, release a dye. With these compounds, compounds which mediate the redox reaction (called electron donors) are preferably used in combination.

Examples of Y effective for this type of compound are those represented by the formula (CXII):

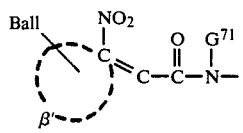
(CXII)

wherein Ball and $\beta'$ are the same as defined for those in the general formula (CIII), and $G^{71}$ represents an alkyl group (including a substituted alkyl group). Specific examples of this type of Y are described in Japanese Patent Application (OPI) Nos. 35533/78 and 110827/78.

Further examples of Y suited for this type of compound are those which are represented by (CXIII):

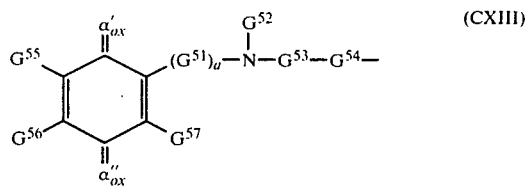
(CXIII)

wherein $\alpha'_{ox}$ and $\alpha''_{ox}$ represent groups capable of giving $\alpha'$ and $\alpha''$, respectively, upon reduction, and $\alpha'$, $\alpha''$, $G^{51}$ $G^{52}$, $G^{53}$, $G^{54}$, $G^{55}$, $G^{56}$, $G^{57}$ and a are the same as defined with respect to formula (CVIII). Specific examples of Y described above are described in Japanese Patent Application (OPI) No. 110827/78, U.S. Pat. Nos. 4,356,249 and 4,358,525.

Further examples of Y suited for this type of compound are those which are represented by the formulae (CXIV-A) and (CXIV-B):

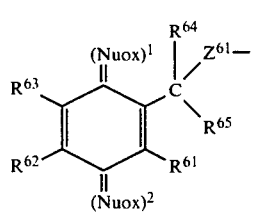
(CXIV-A)

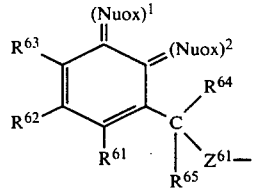
(CXIV-B)

wherein $(Nuox)^1$ and $(Nuox)^2$, which may be the same or different, each represents an oxidized nucleophilic group, and other notations are the same as defined with respect to the formulae (CIX) and (CX). Specific examples of this type of Y are described in Japanese Patent Application (OPI) Nos. 130927/79 and 164342/81.

The publicly known documents having been referred to with respect to (CXII), (CXIII), (CXIV-A) and (CXIV-B) describe electron donors to be used in combination.

As still further different type of compound represented by the general formula (CI), there are illustrated LDA compounds (Linked Donor Acceptor Compounds). These compounds are dye providing nondiffusible substances which cause donor-acceptor reaction in the presence of a base to release a diffusible dye but, upon reaction with an oxidation product of a developing agent, they substantially do not release the dye any more.

Examples of Y effective for this type of compound are those represented by the formula (CXV) (specific examples thereof being described in Japanese Patent Application (OPI) No. 60289/83):

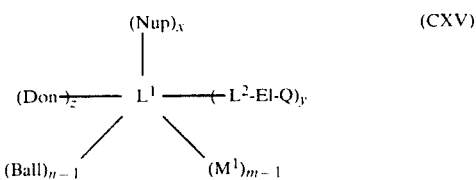

(CXV)

wherein n, x, y and z each represents 1 or 2, m represents an integer of 1 or more; Don represents a group containing an electron donor or its precursor moiety; $L^1$ represents an organic group linking Nup to —El—Q or Don; Nup represents a precursor of a nucleophilic group; El represents an electrophilic center; Q represents a divalent group; Ball represents a ballast group; $L^2$ represents a linking group; and $M^1$ represents an optional substituent.

The ballast group is an organic ballast group which can render the dye providing substance nondiffusible, and is preferably a group containing a $C_{8-32}$ hydrophobic group. Such organic ballast group is bound to the dye providing substance directly or through a linking group (e.g., an imino bond, an ether bond, a thioether bond, a carbonamido bond, a sulfonamido bond, a ureido bond, an ester bond, an imido bond, a carbamoyl bond, a sulfamoyl bond, etc., and combination thereof).

Two or more kinds of the dye providing substances can be employed together. In such a case two or more kinds of the dye providing substances may be used together in order to provide the same hue or in order to reproduce black color.

The dye providing redox compound used in the present invention can be introduced into a layer of the light-sensitive material by known methods such as the method as described in U.S. Pat. No. 2,322,027. In this case, an organic solvent having a high boiling point or an organic solvent having a low boiling point as described below can be used. For example, the dye releasing redox compound is dispersed in a hydrophilic colloid after dissolved in an organic solvent having a high boiling point, for example, a phthalic acid alkyl ester (for example, dibutyl phthalate, dioctyl phthalate, etc.), a phosphoric acid ester (for example, diphenyl phosphate, triphenyl phosphate, tricresyl phosphate, dioctylbutyl phosphate, etc.), a citric acid ester (for example, tributyl acetylcitrate, etc.), a benzoic acid ester (for example, octyl benzoate, etc.), an alkylamide (for example, diethyl laurylamide, etc.), an aliphatic acid ester (for example, dibutoxyethyl succinate, dioctyl azelate, etc.), a trimesic acid ester (for example, tributyl trimesate, etc.), etc., or an organic solvent having a boiling point of about 30° C. to 160° C., for example, a lower alkyl acetate such as ethyl acetate, butyl acetate, etc., ethyl propionate, secondary butyl alcohol, methyl isobutyl ketone, β-ethoxyethyl acetate, methyl cellosolve acetate, cyclohexanone, etc. The above described organic solvents having a high boiling point and organic solvents having a low boiling point may be used as a mixture thereof.

Further, it is possible to use a dispersion method using a polymer as described in Japanese Patent Publication No. 39853/76 and Japanese Patent Application (OPI) No. 59943/76. Moreover, various surface active agents can be used when the dye providing substance is dispersed in a hydrophilic colloid. For this purpose, the surface active agents illustrated in other part of the specification can be used.

In the present invention, if necessary, a reducing agent may be used. The reducing agents used in the present invention include the following compounds.

Hydroquinone compounds (for example, hydroquinone, 2,5-dichlorohydroquinone, 2-chlorohydroquinone, etc.), aminophenol compounds (for example, 4-aminophenol, N-methylaminophenol, 3-methyl-4-aminophenol, 3,5-dibromoaminophenol, etc.), catechol compounds (for example, catechol, 4-cyclohexylcatechol, 3-methoxycatechol, 4-(N-octadecylamino)catechol, etc.), phenylenediamine compounds (for example, N,N-diethyl-p-phenylenediamine, 3-methyl-N,N-diethyl-p-phenylenediamine, 3-methoxy-N-ethyl-N-ethoxy-p-phenylenediamine, N,N,N',N'-tetramethyl-p-phenylenediamine, etc.).

Various combinations of developing agents as described in U.S. Pat. No. 3,039,869 can also be used.

In the present invention, an amount of the reducing agent added is from 0.01 mol to 20 mols per mol of silver and more preferably from 0.1 mol to 10 mols per mol of silver.

The silver halide used in the present invention includes silver chloride, silver chlorobromide, silver chloroiodide, silver bromide, silver iodobromide, silver chloroiodobromide and silver iodide, etc.

The process for preparing those silver halides is explained taking the case of silver iodobromide. That is, the silver iodobromide is prepared by first adding silver nitrate solution to potassium bromide solution to form silver bromide particles and then adding potassium iodide to the mixture.

Two or more kinds of silver halides in which a particle size and/or a halogen composition are different from each other may be used in mixture.

An average particle size of the silver halide used in the present invention is preferably from 0.001 μm to 10 μm and more preferably from 0.001 μm to 5 μm.

The silver halide used in the present invention may be used as is. However, it may be chemically sensitized with a chemical sensitizing agent such as compounds of sulfur, selenium or tellurium, etc., or compounds of gold, platinum, palladium, rhodium or iridium, etc., a reducing agent such as tin halide, etc., or a combination thereof. The details thereof are described in T. H. James, *The Theory of the Photographic Process*, The Fourth Edition, Chapter 5, pages 149–169.

In the particularly preferred embodiment of the present invention, an organic silver salt oxidizing agent is used together. The organic silver salt oxidizing agent is a silver salt which forms a silver image by reacting with the above described image forming substance or a reducing agent coexisting, if necessary, with the image forming substance, when it is heated to a temperature of above 80° C. and, preferably, above 100° C. in the presence of exposed silver halide. By coexisting the organic silver salt oxidizing agent, the light-sensitive material which provides higher color density can be obtained.

Examples of such organic silver salt oxidizing agents include those described in U.S. Pat. No. 4,500,626.

A silver salt of an organic compound having a carboxyl group can be used. Typical examples thereof include a silver salt of an aliphatic carboxylic acid and a silver salt of an aromatic carboxylic acid.

In addition, a silver salt of a compound containing a mercapto group or a thione group and a derivative thereof can be used.

Further, a silver salt of a compound containing an imino group can be used. Examples of these compounds include a silver salt of benzotriazole and a derivative thereof as described in Japanese Patent Publication Nos. 30270/69 and 18416/70, for example, a silver salt of benzotriazole, a silver salt of alkyl substituted benzotriazole such as a silver salt of methylbenzotriazole, etc., a silver salt of a halogen substituted benzotriazole such as a silver salt of 5-chlorobenzotriazole, etc., a silver salt of carboimidobenzotriazole such as a silver salt of butylcarboimidobenzotriazole, etc., a silver salt of 1,2,4-triazole or 1-H-tetrazole as described in U.S. Pat. No. 4,220,709, a silver salt of carbazole, a silver salt of saccharin, a silver salt of imidazole and an imidazole derivative, and the like.

Moreover, a silver salt as described in *Research Disclosure*, Vol. 170, No. 17029 (June, 1978) and an organic metal salt such as copper stearate, etc., are the organic metal salt oxidizing agent capable of being used in the present invention.

Methods of preparing these silver halide and organic silver salt oxidizing agents and manners of blending them are described in *Research Disclosure*, No. 17029, Japanese Patent Application (OPI) Nos. 32928/75 and 42529/76, U.S. Pat. No. 3,700,458, and Japanese Patent Application (OPI) Nos. 13224/74 and 17216/75.

A suitable coating amount of the light-sensitive silver halide and the organic silver salt oxidizing agent employed in the present invention is in a total of from 50 mg/m$^2$ to 10 g/m$^2$ calculated as an amount of silver.

The binder which can be used in the present invention can be employed individually or in a combination thereof. A hydrophilic binder can be used as the binder according to the present invention. The typical hydrophilic binder is a transparent or translucent hydrophilic colloid, examples of which include a natural substance, for example, protein such as gelatin, a gelatin derivative, a cellulose derivative, etc., a polysaccharide such as starch, gum arabic, etc., and a synthetic polymer, for example, a water-soluble polyvinyl compound such as polyvinyl alcohol, polyvinyl pyrrolidone, acrylamide polymer, etc. Another example of the synthetic polymer compound is a dispersed vinyl compound in a latex form which is used for the purpose of increasing dimensional stability of a photographic material.

Further, in the present invention, it is possible to use a compound which activates development simultaneously while stabilizing the image. Particularly, it is preferred to use isothiuroniums including 2-hydroxyethylisothiuronium trichloroacetate as described in U.S. Pat. No. 3,301,678, bisisothiuroniums including 1,8-(3,6-dioxaoctane)-bis(isothiuronium trifluoroacetate), etc., as described in U.S. Pat. No. 3,669,670, thiol compounds as described in German Patent Application (OLS) No. 2,162,714, thiazolium compounds such as 2-amino-2-thiazolium trichloroacetate, 2-amino-5-bromoethyl-2-thiazolium trichloroacetate, etc., as described in U.S. Pat. No. 4,012,260, compounds having α-sulfonylacetate as an acid part such as bis(2-amino-2-thiazolium)methylenebis(sulfonylacetate), 2-amino-2-thiazolium phenylsulfonylacetate, etc., as described in U.S. Pat. No. 4,060,420, and compounds having 2-carboxycarboxamide as an acid part as described in U.S. Pat. No. 4,088,496.

The photosensitive material of the present invention can contain a toning agent as occasion arises. Effective toning agents are 1,2,4-triazoles, 1H-tetrazoles, thiouracils, 1,3,4-thiadiazoles, and like compounds. Examples of preferred toning agents include 5-amino-1,3,4-thiadiazole-2-thiol, 3-mercapto-1,2,4-triazole, bis(dimethylcarbamyl)disulfide, 6-methylthiouracil, 1-phenyl-2-tetrazoline-5-thione, and the like. Particularly effective toning agents are compounds which can impart a black color tone to images.

The content of such a toning agent as described above, though depending upon the kind of a heat developable photosensitive material used, processing conditions, desired images and various other factors, generally ranges from about 0.001 to 0.1 mol per mol of silver in the photosensitive material.

The above described bases or base precursors can be used not only for the acceleration of dye release but also for other purposes such as the control of a pH value.

The above described various ingredients to constitute a heat developable photosensitive material can be arranged in arbitrary positions, if desired. For instance, one or more of the ingredients can be incorporated in one or more of the constituent layers of a photosensitive material, if desired. In some cases, it is desired that particular portions of reducing agent, image stabilizing agent and/or other additives should be distributed in a protective layer. As a result of the distribution in the above described manner, migration of additives among constituent layers of a heat developable photosensitive material can be reduced. Therefore, such distribution of additives is of advantage to some cases.

The heat developable photosensitive materials of the present invention are effective in forming both negative and positive images. The negative or positive image can be formed depending mainly on the type of the light-sensitive silver halide. For instance, in order to produce direct positive images, internal image type silver halide emulsions described in U.S. Pat. Nos. 2,592,250, 3,206,313, 3,367,778 and 3,447,927, or mixtures of surface image type silver halide emulsions with internal image type silver halide emulsions as described in U.S. Pat. No. 2,996,382 can be used.

Various means of exposure can be used in the present invention. Latent images are obtained by imagewise exposure by radiant rays including visible rays. Generally, light sources used for conventional color prints can be used, examples of which include tungsten lamps, mercury lamps, halogen lamps such as iodine lamps, xenon lamps, laser light sources, CRT light sources, fluorescent tubes and light emitting diodes, etc.

In the present invention, after the heat developable color photographic material is exposed to light, the resulting latent image can be developed by heating the whole material to a suitably elevated temperatures. A higher temperature or lower temperature can be utilized to prolong or shorten the heating time, if it is within the above described temperature range.

As the heating means, a simple heat plate, iron, heat roller, heat generator utilizing carbon or titanium white, etc., or analogues thereof may be used.

The silver halide used in the present invention can be spectrally sensitized with methine dyes or other dyes. Suitable dyes which can be employed include cyanine dyes, merocyanine dyes, complex cyanine dyes, complex merocyanine dyes, holopolar cyanine dyes, hemicyanine dyes, stytyl dyes, and hemioxonol dyes. Of these dyes, cyanine dyes, merocyanine dyes and complex merocyanine dyes are particularly useful. Any conventionally utilized nucleus for cyanine dyes, such as basic heterocyclic nuclei, is applicable to these dyes. This is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei may also be substituted.

To merocyanine dyes and complex merocyanine dyes, as nuclei having a ketomethylene structure, 5- or 6-membered heterocyclic nuclei such as a pyrazoline-5-one nucleus, a thiohydantoin nucleus, a 2-thiooxazolidin-2,4-dione nucleus, a thiazolidin-2,4-dione nucleus, a rhodanine nucleus, a thiobarbituric acid nucleus, etc., may also be applicable.

These sensitizing dyes can be employed individually, and can also be employed in combination thereof. A combination of sensitizing dyes is often used, particularly for the purpose of supersensitization. Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, Japanese Patent Application (OPI) Nos. 110618/77 and 109925/77, etc.

The sensitizing dyes may be present in the emulsion together with dyes which themselves do not give rise to spectrally sensitizing effects but exhibit a supersensitizing effect or materials which do not substantially absorb visible light but exhibit a super-sensitizing effect. For example, aminostilbene compounds substituted with a nitrogen-containing heterocyclic group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, etc., can be present. The combinations described in U.S. Pat. Nos. 3,615,613, 3,615,641, 3,617,295 and 3,635,721 are particularly useful.

A support used in the light-sensitive material and the dye fixing material employed, if desired, according to the present invention is that which can endure at the processing temperature. As an ordinary support, not only glass, paper, metal or analogues thereof may be used, but also an acetyl cellulose film, a cellulose ester film, a polyvinyl acetal film, a polystyrene film, a polycarbonate film, a polyethylene terephthalate film, and a film related thereto or a plastic material may be used. Further, a paper support laminated with a polymer such as polyethylene, etc., can be used. The polyesters described in U.S. Pat. Nos. 3,634,089 and 3,725,070 are preferably used.

In the photographic light-sensitive material and the dye fixing material of the present invention, the photographic emulsion layer and other binder layers may contain inorganic or organic hardeners. It is possible to use chromium salts (chromium alum, chromium acetate, etc.), aldehydes (formaldehyde, glyoxal, glutaraldehyde, etc.), N-methylol compounds (dimethylolurea, methylol dimethylhydantoin, etc.), dioxane derivatives (2,3-dihydroxydioxane, etc.), active vinyl compounds (1,3,5-triacryloyl-hexahydro-s-triazine, 1,3-vinylsulfonyl-2-propanol, etc.), active halogen compounds (2,4-dichloro-6-hydroxy-s-triazine, etc.), mucohalogenic acids (mucochloric acid, mucophenoxychloric acid, etc.), etc., which are used alone or as a combination thereof.

The transfer of dyes from the light-sensitive layer to the dye fixing layer can be carried out using a dye transfer assistant.

The dye transfer assistants suitably used in a process wherein it is supplied from the outside include water and an aqueous solution containing sodium hydroxide, potassium hydroxide or an inorganic alkali metal salt. Further, a solvent having a low boiling point such as methanol, N,N-dimethylformamide, acetone, diisobutyl ketone, etc., and a mixture of such a solvent having a low boiling point with water or an alkaline aqueous solution can be used. The dye transfer assistant may be used by wetting the image receiving layer with the transfer assistant.

When the dye transfer assistant is incorporated into the light-sensitive material or the dye fixing material, it is not necessary to supply the transfer assistant from the outside. In this case, the above described dye transfer assistant may be incorporated into the material in the form of water of crystallization or microcapsules or as a precursor which releases a solvent at a high temperature.

More preferred process is a process wherein a hydrophilic thermal solvent which is solid at an ambient temperature and melts at a high temperature is incorporated into the light-sensitive material or the dye fixing material. The hydrophilic thermal solvent can be incorporated either into any of the light-sensitive material and the dye fixing material or into both of them. Although the solvent can be incorporated into any of the emulsion layer, the interlayer, the protective layer and the dye fixing layer, it is preferred to incorporate it into the dye fixing layer and/or adjacent layers thereto.

Examples of the hydrophilic thermal solvents include ureas, pyridines, amides, sulfonamides, imides, alcohols, oximes and other heterocyclic compounds.

Other compounds which can be used in the photosensitive material of the present invention, for example, sulfamide derivatives, cationic compounds containing a pyridinium group, surface active agents having polyethylene oxide chains, sensitizing dye, antihalation and anti-irradiation dyes, hardeners, mordants and so on, are those described in U.S. Pat. Nos. 4,500,626, 4,478,927, 4,463,079, and Japanese Patent Application Nos. 28928/83 (corresponding to U.S. patent application Ser. No. 582,655, filed on Feb. 23, 1984) and U.S. Pat. No. 4,503,137. Methods for the exposure and so on cited in the above described patents can be employed in the present invention also.

The present invention will be explained in greater detail with reference to the following examples, but the present invention should not be construed as being limited thereto. Unless otherwise indicated, all percents, ratios, etc., are by weight.

EXAMPLE 1

Preparation of Silver Iodobromide Emulsion 40 g of gelatin and 26 g of potassium bromide (KBr) were dissolved in 3,000 ml of water and the solution was maintained at 50° C. with stirring. A solution of 34 g of silver nitrate dissolved in 200 ml of water and 200 ml of a solution of 0.02 g of Dye I described below dissolved in 300 ml of methanol were simultaneously added to the above prepared solution over a 10 minute period. Then, a solution of 3.3 g of potassium iodide (KI) dissolved in 100 ml of water was added over a 2 minute period. The thus prepared silver iodobromide emulsion was adjusted in pH, precipitated, and freed of excess salts. It was then adjusted to a pH of 6.0, thereby 400 g of a silver iodobromide emulsion was obtained.

Dye I:

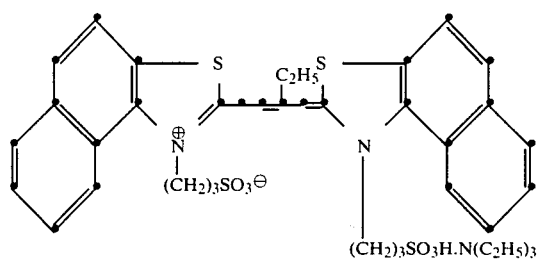

Preparation of Dispersion of Coupler in Gelatin

A mixture of 5 g of 2-dodecylcarbamoyl-1-naphthol, 0.5 g of sodium 2-ethylhexyl sulfosuccinate, 2.5 g of tricresyl phosphate (TCP) and 30 ml of ethyl acetate was dissolved. This solution was mixed with 100 g of a 10% aqueous solution of gelatin with stirring and the mixture was dispersed by means of a homogenizer at 10,000 rpm for 10 minutes.

Preparation of Light-Sensitive Material

A coating solution which had been prepared by adding a base precursor shown in Table 1 below to the composition shown below was coated on a polyethylene terephthalate support at a wet layer thickness of 60 μm and dried to prepare a light-sensitive material.

| | | |
|---|---|---|
| (a) | Silver iodobromide emulsion | 10 g |
| (b) | Dispersion of coupler in gelatin | 3.5 g |
| (c) | Gelatin (10% aqueous solution) | 5 g |
| (d) | Solution containing 0.2 g of 2,6-dichloro-p-aminophenol dissolved in 17 ml of water | |

The light-sensitive materials thus obtained were each exposed imagewise at 2,000 lux for 5 seconds using a tungsten lamp and then uniformly heated for 20 seconds on a heat block which had been heated at 150° C., whereby negative cyan color images were obtained.

Further, the light-sensitive materials were each preserved at 60° C. for 2 days and then subjected to light exposure and development in the same manner as described above to obtain negative cyan color images.

The densities of these cyan color images were measured using a Macbeth transmission densitometer (TD-504), and the results thus obtained are shown in Table 1.

TABLE 1

| Base Precursor | Amount Added (g) | Fresh | | After Lapse of 2 Days at 60° C. | |
|---|---|---|---|---|---|
| | | $D_{max}$ | $D_{min}$ | $D_{max}$ | $D_{min}$ |
| (3) (Present Invention) | 0.21 | 2.18 | 0.15 | 2.13 | 0.30 |
| (7) (Present Invention) | 0.25 | 2.17 | 0.13 | 2.11 | 0.24 |
| (11) (Present Invention) | 0.18 | 1.94 | 0.16 | 1.89 | 0.23 |

TABLE 1-continued

| Base Precursor | Amount Added (g) | Fresh | | After Lapse of 2 Days at 60° C. | |
|---|---|---|---|---|---|
| | | $D_{max}$ | $D_{min}$ | $D_{max}$ | $D_{min}$ |
| Comparison | 0.18 | 2.20 | 0.18 | 2.15 | 1.85 |

The base precursor for comparison used was the following compound.

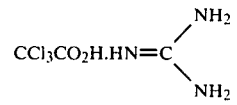

From the results shown in Table 1 above, it is demonstrated that preservability of the light-sensitive material is greatly improved by the use of the base precursor according to the present invention.

EXAMPLE 2

The same silver iodobromide emulsion as described in Example 1 and the following dispersion of dye providing substance were employed.

Preparation of Dispersion of Dye Providing Substance

A mixture of 5 g of Dye Providing Substance (2) shown below, 0.5 g of sodium 2-ethylhexyl sulfosuccinate, as a surface active agent, 5 g of tricresyl phosphate (TCP) and 30 ml ethyl acetate was dissolved by heating at about 60° C. to prepare a uniform solution. This solution was mixed with 100 g of a 10% aqueous solution of gelatin with stirring and the mixture was dispersed by means of a homogenizer at 10,000 rpm for 10 minutes.

Dye Providing Substance (2)

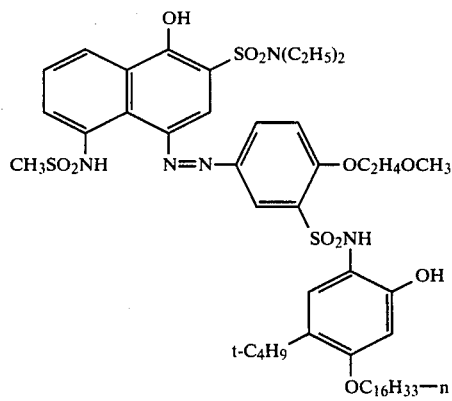

Preparation of Light-Sensitive Material

| | | |
|---|---|---|
| (a) | Light-sensitive silver iodobromide emulsion (same as described in Example 1) | 25 g |
| (b) | Dispersion of Dye Providing Substance (2) | 33 g |
| (c) | 5% Aqueous solution of compound having the following formula: | 10 ml |

$C_9H_{19}$—⟨ ⟩—O(CH$_2$CH$_2$O)$_{10}$—H

| | | |
|---|---|---|
| (d) | 10% Aqueous solution of compound | 4 ml |

-continued

| | | |
|---|---|---|
| | having the following formula H₂NSO₂N(CH₃)₂ | |
| (e) | Water | 20 ml |

The above components (a) to (e) and a base precursor shown in Table 2 below were mixed and dissolved by heating and the mixture was coated on a polyethylene terephthalate film at a wet layer thickness of 30 μm and dried.

The light-sensitive material thus obtained was exposed imagewise at 2,000 lux for 10 seconds using a tungsten lamp and then uniformly heated for 20 seconds on a heat block which had been heated at 150° C.

Preparation of Image Receiving Material Having an Image Receiving Layer 10 g of poly(methyl acrylate-co-N,N,N-trimethyl-N-vinylbenzylammonium chloride) (molar ratio of methyl acrylate to vinylbenzylammonium chloride was 1:1) was dissolved in 200 ml of water and then uniformly mixed with 100 g of a 10% aqueous solution of lime-proxessed gelatin. The resulting mixture was uniformly coated at a wet layer thickness of 90 μm on a paper support laminated with polyethylene with titanium dioxide dispersed therein. The thus prepared material was dried and then used as an image receiving material.

The above described image receiving material was soaked in water and then superimposed on the above heated light-sensitive material in such a manner that their coated layers were in contact with each other.

After heating for 6 seconds on a heat block maintained at 80° C., the image receiving material was separated from the light-sensitive material, whereupon a negative magenta color image was obtained in the image receiving material.

Further, these light-sensitive materials were each preserved at 60° C. for 2 days and then subjected to the same procedure as described above to obtain negative magenta color images.

The densities of these magenta color images were measured using a Macbeth reflection densitometer (RD-519), and the results thus obtained are shown in Table 2.

TABLE 2

| Base Precursor | Amount Added (g) | Fresh $D_{max}$ | Fresh $D_{min}$ | After Lapse of 2 Days at 60° C. $D_{max}$ | After Lapse of 2 Days at 60° C. $D_{min}$ |
|---|---|---|---|---|---|
| (3) (Present Invention) | 2.1 | 2.15 | 0.18 | 2.11 | 0.31 |
| (7) (Present Invention) | 2.5 | 2.13 | 0.14 | 2.08 | 0.28 |
| (11) (Present Invention) | 1.8 | 1.91 | 0.17 | 1.84 | 0.24 |
| Comparison | 1.8 | 2.20 | 0.18 | 2.15 | 1.85 |

The base precursor for comparison above was the same compound as used in Example 1.

These results shown in Table 2 above demonstrate that extremely good color images formed in the light-sensitive material can be transferred into the image receiving material by the use of the light-sensitive material having good preservability according to the present invention.

EXAMPLE 3

In the following, an example using an organic silver salt oxidizing agent is illustrated.

Preparation of Silver Benzotriazole Emulsion 28 g of gelatin and 13.2 g of benzotriazole were dissolved in 3,000 ml of water and the solution was maintained at 40° C. with stirring. A solution of 17 g of silver nitrate dissolved in 100 ml of water was added to the above prepared solution over a 2 minute period. The thus prepared silver benzotriazole emulsion was adjusted in pH, precipitated, and freed of excess salts. It was then adjusted to a pH of 6.0, thereby 400 g of a silver benzotriazole emulsion was obtained.

Using the above described silver benzotriazole emulsion, the following light-sensitive coating composition was prepared.

| | | |
|---|---|---|
| (a) | Silver iodobromide emulsion (same as described in Example 1) | 20 g |
| (b) | Silver benzotriazole emulsion | 10 g |
| (c) | Dispersion of dye providing substance (same as described in Example 2) | 33 g |
| (d) | 5% Aqueous solution of compound having the following formula: | 10 ml |

C₉H₁₉—⟨phenyl⟩—O(CH₂CH₂O)₁₀H

| | | |
|---|---|---|
| (e) | 10% Aqueous solution of compound having the following formula: H₂NSO₂N(CH₃)₂ | 4 ml |
| (f) | Base Precursor (3) according to the present invention | 2.5 g |
| (g) | Dispersion of acid precursor in gelatin shown below | 8 ml |
| (h) | Water | 12 ml |

The dispersion of acid precursor in gelatin described in (g) above was prepared in the following manner.

10 g of the compound shown below was added to 100 g of a 1% aqueous solution of gelatin and the mixture was pulverized in a mill containing 100 g of glass beads with an average diameter of about 0.6 mm for 10 minutes. The glass beads were separated by filtration, and a dispersion of acid precursor in gelatin was obtained.

Acid Precursor:

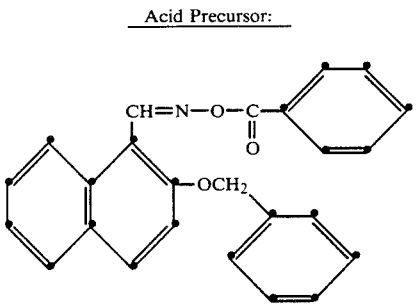

The above components (a) to (h) were mixed, followed by the same procedure as described in Example 2 to prepare a light-sensitive material and then the light-sensitive material was processed and evaluated in the same manner as described in Example 2. The results thus obtained are shown in Table 3.

TABLE 3

| | Fresh | | After Lapse of 2 Days at 60° C. | |
|---|---|---|---|---|
| | $D_{max}$ | $D_{min}$ | $D_{max}$ | $D_{min}$ |
| | 2.21 | 0.19 | 2.18 | 0.31 |

It is demonstrated from the results shown in Table 3 that the light-sensitive material according to the present invention has excellent preservability.

EXAMPLE 4

Preparation of Silver Benzotriazole Emulsion Containing Light-Sensitive Silver Bromide 10 g of gelatin and 6.5 g of benzotriazole were dissolved in 1,000 ml of water and the solution was maintained at 50° C. with stirring. A solution of 8.5 g of silver nitrate dissolved in 100 ml of water was added to the above prepared solution over a 2 minute period. Then, a solution of 1.2 g of potassium bromide dissolved in 50 ml of water was added over a 2 minute period. The thus prepared emulsion was adjusted in pH, precipitated, and freed of excess salts. It was then adjusted to a pH of 6.0, thereby 200 g of a silver benzotriazole emulsion containing silver bromide was obtained.

Preparation of Dispersion of Dye Providing Substance in Gelatin

A mixture of 10 g of a dye providing substance shown below, 0.5 g of sodium 2-ethylhexyl sulfosuccinate, as a surface active agent, 4 g of tricresyl phosphate (TCP) and 20 ml of cyclohexanone was dissolved by heating at about 60° C. to prepare a uniform solution. This solution was mixed with 100 g of a 10% aqueous solution of lime-processed gelatin with stirring and the mixture was dispersed by means of a homogenizer at 10,000 rpm for 10 minutes.

Dye Providing Substances:

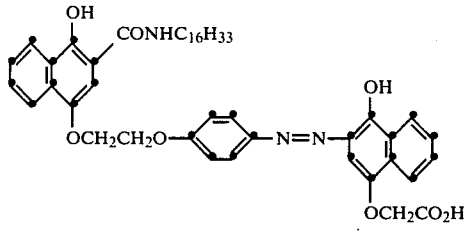

Preparation of Light-Sensitive Coating Composition

| (a) Silver benzotriazole emulsion containing light-sensitive silver bromide | 10 g |
|---|---|
| (b) Dispersion of dye providing substance | 3.5 g |
| (c) Base Precursor (3) according to the present invention | 0.28 g |
| (d) Gelatin (10% aqueous solution) | 5 g |
| (e) Solution containing 200 mg of 2,6-dichloro-4-aminophenol dissolved in 4 ml of methanol | |

The above components (a) to (e) were mixed and dissolved by heating and the mixture was coated on a polyethylene terephthalate film having a thickness of 180 μm at a wet layer thickness of 30 μm and dried.

The light-sensitive material thus obtained was exposed imagewise at 2,000 lux for 5 seconds using a tungsten lamp and then uniformly heated for 20 seconds on a heat block which had been heated at 150° C.

The same procedure as described in Example 2 was conducted using the image receiving material as described in Example 2, and a negative magenta color image was obtained in the image receiving material.

The density of the negative image was measured by means of a Macbeth reflection densitometer (RD-519). The maximum density was 1.99 and the minimum density was 0.22. These results demonstrate that the compound according to the present invention exhibits an excellent effect.

EXAMPLE 5

Preparation of Dispersion of Dye Providing Substance in Gelatin

A mixture of 5 g of a reducible dye releasing agent shown below, 4 g of an electron donative substance shown below, 0.5 g of sodium 2-ethylhexyl sulfosuccinate, 10 g of tricresyl phosphate (TCP) and 20 ml of cyclohexanone was dissolved by heating at about 60° C. to prepare a uniform solution. This solution was mixed with 100 g of a 10% aqueous solution of gelatin with stirring and the mixture was dispersed by means of a homogenizer at 10,000 rpm for 10 minutes.

Reducible Dye Releasing Agent

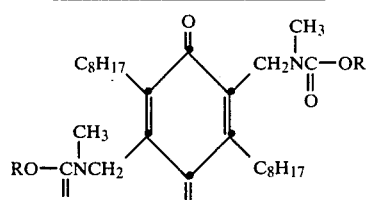

wherein R represents a group having the following structure:

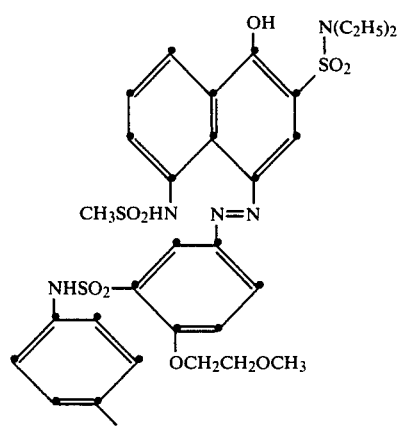

Electron Donative Substance

-continued

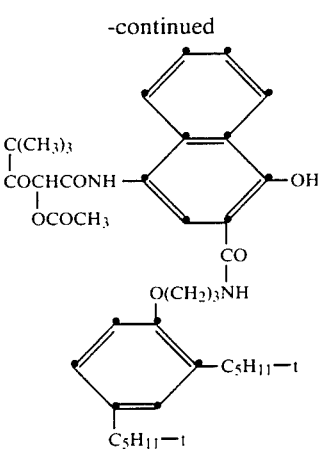

Preparation of Light-Sensitive Coating Composition

| | | |
|---|---|---|
| (a) | Silver benzotriazole emulsion containing light-sensitive silver bromide (same as described in Example 4) | 10 g |
| (b) | Dispersion of dye providing substance (described above) | 3.5 g |
| (c) | Base Precursor (3) according to the present invention | 0.4 g |
| (d) | 5% Aqueous solution of a compound having the following formula: | 1.5 ml |

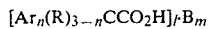

The above components (a) to (d) and 4 ml of water were mixed and dissolved by heating and the mixture was coated on a polyethylene terephthalate film at a wet layer thickness of 30 μm and dried to prepare a light-sensitive material.

The light-sensitive material thus obtained was exposed imagewise at 2,000 lux for 10 seconds using a tungsten lamp and then uniformly heated for 40 seconds on a heat block which had been heated at 140° C.

The same image receiving material as described in Example 2 was soaked in water and then superimposed on the above heated light-sensitive material in such a manner that their coated layers were in contact with each other.

The density of the positive magenta color image obtained in the image receiving material was measured by means of a Macbeth reflection densitometer (RD-519). The maximum density and minimum density to green light were 1.97 and 0.31, respectively.

These results demonstrate the effectiveness of the base precursor according to the present invention.

While the invention has been described in detail and with reference to specific embodiments thereof, it will be apparent to one skilled in the art that various changes and modifications can be made therein without departing from the spirit and scope thereof.

What is claimed is:

1. A heat developable light-sensitive material containing a base precursor compound represented by the general formula (I):

$$[Ar_n(R)_{3-n}CCO_2H]_l \cdot B_m \qquad (I)$$

wherein Ar represents an aryl group or a heterocyclic group; R represents a substituent selected from the group consisting of a hydrogen atom, a silyl group, an alkyl group, an alkenyl group, an alkynyl group, an aralkyl group, a cycloalkyl group, an alkoxy group, an aryloxy group, an alkylthio group, an arylthio group and a hydroxy group; Ar and R may be bonded in a part thereof to form a ring; B represents a mono- or diacidic base which has a pKa of 7 or more and contains 12 or less carbon atoms; n represents an integer from 1 to 3; l and m each represents an integer of 1 or 2 and maintain a relationship in that a number of positive charge and a number of negative charge are equal; when n represents 1 or 2, two R's or Ar's may be the same or different, when n represents 3, three Ar's may be the same or different, and the substituent represented by Ar or R may be further substituted with a substituent.

2. A heat developable light-sensitive material as claimed in claim 1, wherein Ar represents a substituted aryl group or a substituted heterocyclic group substituted with an electron withdrawing group having a Hammett's σ value of 0 or greater.

3. A heat developable light-sensitive material as claimed in claim 2, wherein the electron withdrawing group is a halogen atom, a nitro group, a cyano group or an acyl group.

4. A heat developable light-sensitive material as claimed in claim 1, wherein B represents an organic base having a pKa of 9 or more and a boiling point of 100° C. or higher.

5. A heat developable light-sensitive material as claimed in claim 1, wherein B represents an organic base having a pKa of 10 or more and being substantially nonvolatile at normal temperature and free from a bad smell.

6. A heat developable light-sensitive material as claimed in claim 1, wherein the organic base represented by B is a guanidine, a cyclic guanidine, an amidine or a cyclic amidine.

7. A heat developable light-sensitive material as claimed in claim 1, wherein the organic base represented by B is hydrophilic.

8. A heat developable light-sensitive material as claimed in claim 1, wherein the organic base represented by B has 10 or less carbon atoms in total.

9. A heat developable light-sensitive material as claimed in claim 1, wherein the base precursor is present in an amount of 50% by weight or less based on the coated amount of a layer to be incorporated.

10. A heat developable light-sensitive material as claimed in claim 1, wherein the base precursor is present in an amount of from 0.01% by weight to 40% by weight based on the coating amount of a layer to be incorporated.

11. A heat developable light-sensitive material as claimed in claim 1, wherein the material contains a silver halide emulsion.

12. A heat developable light-sensitive material as claimed in claim 11, wherein the material further contains an organic silver salt oxidizing agent.

13. A heat developable light-sensitive material as claimed in claim 11, wherein the silver halide emulsion is a spectrally sensitized silver halide emulsion.

14. A heat developable light-sensitive material as claimed in claim 11, wherein the material further contains an image forming substance.

15. A heat developable light-sensitive material as claimed in claim 14, wherein the image forming substance is a coupler capable of forming a color image by bonding to an oxidation product of a developing agent.

16. A heat developable light-sensitive material as claimed in claim 14, wherein the image forming substance is a dye providing substance.

17. A heat developable light-sensitive material as claimed in claim 16, wherein the dye providing substance is a compound represented by the following formula (CI):

wherein q represents 1 or 2, when q represents 2, Dye—X's may be the same or different; Dye represents a dye which becomes mobile when it is released from the molecule of the compound represented by the formula (CI); X represents a simple bond or a connecting group; and Y represents a group which releases Dye in corresponding or countercorresponding to light-sensitive silver salts having a latent image distributed imagewise, the diffusibility of a dye released being different from that of the compound represented by Dye—X—Y.

18. A heat developable light-sensitive material as claimed in claim 17, wherein Dye represents a dye having a hydrophilic group.

19. A heat developable light-sensitive material as claimed in claim 17, wherein the dye represented by Dye is an azo dye, an azomethine dye, an anthraquinone dye, a naphthoquinone dye, a styryl dye, a nitro dye, a quinoline dye, a carbonyl dye or a phthalocyanine dye.

20. A heat developable light-sensitive material as claimed in claim 17, wherein the connecting group represented by X is —NR— (wherein R represents a hydrogen atom, an alkyl group, or a substituted alkyl group), —SO$_2$—, —CO—, an alkylene group, a substituted alkylene group, a phenylene group, a substituted phenylene group, a naphthylene group, a substituted naphthylene group, —O—, —SO—, or a group derived by combining together two or more of the foregoing groups.

* * * * *